(12) United States Patent
Peters et al.

(10) Patent No.: US 8,152,784 B2
(45) Date of Patent: Apr. 10, 2012

(54) METHOD FOR TREATING OR PREVENTING STEROID-INDUCED GLAUCOMA

(75) Inventors: Donna M. Peters, Middleton, WI (US); Mark S. Filla, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1389 days.

(21) Appl. No.: 11/361,343

(22) Filed: Feb. 24, 2006

(65) Prior Publication Data

US 2006/0212008 A1    Sep. 21, 2006

Related U.S. Application Data

(60) Provisional application No. 60/655,735, filed on Feb. 24, 2005.

(51) Int. Cl.
    *A61M 35/00* (2006.01)

(52) U.S. Cl. ......................... 604/294; 424/427

(58) Field of Classification Search .................. 604/290, 604/294–300; 424/427; 514/2, 12, 44
    See application file for complete search history.

(56) References Cited

U.S. PATENT DOCUMENTS

| | | | |
|---|---|---|---|
| 5,595,911 A * | 1/1997 | Tonks ......................... | 435/320.1 |
| 2003/0198971 A1 * | 10/2003 | Balint et al. ...................... | 435/6 |
| 2004/0175377 A1 * | 9/2004 | Peters et al. ............... | 424/94.63 |
| 2005/0043233 A1 * | 2/2005 | Stefanic et al. .................. | 514/12 |

OTHER PUBLICATIONS

Sharma, A. et al, "Crystal Structure of a heparin- and integrin- binding segment of human fibronectin", The EBMO Journal,18:6, 1468-1479, 1999.*
Rao et al., "Modulation of Aqueous Humor Outflow Facility by the Rho-kinase-Specific Inhibitor Y-27632", Invest. Ophthalmol. Vis. Sci. 42 (5): 1029-1037.*
Kilarski et al, "Inactivation of Src family kinase inhibits angiogenesis in vivo: Implications for a mechanism involving organization of the actin cytoskeleton", Experimental Cell Research, 291: 70-82.*
Flugel-Koch, C. et al, "Thrombospondin-1 in the trabecular meshwork: localization in normal and glaucomatous eyes, and induction by TGF-(beta)1 and dexamethasone in vitro", Experimental Eye Research, 79:649-663, 2004.*
Kilarski et al, "Inactivation of Src family kinase inhibits angiogenesis in vivo: Implications for a mechanism involving organization of the actin cytoskeleton", Experimental Cell Research, 291: 70-82, 2003.*
Rao et al., "Modulation of Aqueous Humor Outflow Facility by the Rho-kinase-Specific Inhibitor Y-27632", Invest. Ophthalmol. Vis. Sci. 42 (5): 1029-1037, 2001.*
Clark, A.F. et al, "Glucocorticoid-Induced Formation of Cross-linked Actin Networks in Cultured Human Trabecular Meshwork Cells", Invest Ophthalmol Vis Sci, 35: 281-294. (Jan. 1994).*
Clark, A.F. et al, "Glucocorticoid-Induced Formation of Cross-linked Actin Networks in Cultured Human Trabecular Meshwork Cells", Invest Ophthalmol Vis Sci, 35:281-294. (Jan. 1994).*
Alpin A, et al., "Signal transduction and signal modulation by cell adhesion receptors: the role of integrins, cadherins, immunoglobulin-cell adhesion molecules, and selectins," Pharm. Rev. 50:197-263 (1998).
Brakebusch C & Fässler R, "The integrin-actin connection, an eternal love affair," EMBO J. 22:2324-2333 (2003).
Cheng S, et al., "Regulation of avb3 and avb5 integrins by dexamethasone in normal human osteoblastic cells," J. Cell. Biochem. 77:265-276 (2000).
Clark A, et al., "Glucocorticoid-induced formation of cross-linked actin networks in cultured human trabecular meshwork cells," Invest. Ophth. & Visual Sci. 35:281-294 (1994).
Clark A, et al., "Dexamethasone alters F-actin architecture and promotes cross-linked actin network formation in human trabecular meshwork tissue," Cell Motility & the Cytoskeleton 60:83-95 (2005).
Dickerson J, et al., "The effect of dexamethasone on integrin and laminin expression in cultured human trabecular meshwork cells," Exp. Eye Res. 66:731-738 (1998).
Gutheil J, et al., "Targeted antiangiogenic therapy for cancer using vitaxin: a humanized monoclonal antibody to the integrin avb3," Clin. Cancer Res. 6:3056-3061 (2000).
Hu Y, et al., "Monkey organ-cultured anterior segments: technique and response to H-7," Exp. Eye Res. 82:1100-1108 (2006).
Ishibashi T, et al., "cDNA microarray analysis of gene expression changes induced by dexamethasone in cultured human trabecular meshwork cells," Invest. Ophthalmology & Visual Sci. 43:3691-3697 (2002).
Mousa S, "alpha v vitronectin receptors in vascular-mediated disorders," Med. Res. Reviews 23:190-199 (2003).
Shimaoka M & Springer T, "Thereapeutic antagonists and conformational regulation of integrin function," Nat. Rev. Drug Discov. 2:703-716 (2003).
Wordinger R & Clark A, "Effects of Glucocortiocoids on the trabecular meshwork: towards a better understanding of glaucoma," Progress in Retinal and Eye Research 18:629-667 (1999).
Zhou L, et al., "Glucocorticoids effects on extracellular matrix proteins and integrins in bovine trabecular meshwork cells in relation to glaucoma," Int. J. Mol. Med. 1:339-346 (1998).

* cited by examiner

*Primary Examiner* — Melanie Hand
(74) *Attorney, Agent, or Firm* — Quarles & Brady LLP

(57) ABSTRACT

An integrin antagonist reduces the occurrence of cross-linked actin network (CLAN) structures in cells of the trabecular meshwork. CLAN structures are associated with steroid-induced glaucoma. Reduction in CLAN structures is associated with increased aqueous humor outflow facility from the trabecular meshwork.

9 Claims, No Drawings

METHOD FOR TREATING OR PREVENTING STEROID-INDUCED GLAUCOMA

CROSS-REFERENCE TO RELATED APPLICATIONS

This application claims the benefit of U.S. Provisional Patent Application No. 60/655,735, filed Feb. 24, 2005, incorporated herein by reference as if set forth in its entirety.

STATEMENT REGARDING FEDERALLY SPONSORED RESEARCH OR DEVELOPMENT

This invention was made with United States government support awarded by the following agency: NIH Grants EY012515 and EY02698. The United States government has certain rights in this invention.

BACKGROUND OF THE INVENTION

The invention relates generally to a method for modulating intraocular pressure (IOP) in an eye of a human or a non-human mammalian subject having or susceptible to steroid-induced glaucoma, and more particularly to a method for modulating an actin cytoskeleton structures in trabecular meshwork cells in a subject having steroid-induced glaucoma.

The front of a mammalian eye has an anterior chamber, bounded at the front by a cornea and at the back by a lens, as well as a posterior chamber located behind an iris but in front of the lens. Behind the iris is a ciliary body that continuously produces aqueous humor, a thin, watery fluid that fills the anterior and posterior chambers. The aqueous humor nourishes the cornea and the lens and gives the front of the eye its form and shape. The aqueous humor flows from the ciliary body through the pupil and through a trabecular meshwork then through the canal of Schlemm. The trabecular meshwork is the complex tissue located in the angle between the cornea and the iris that contains specialized endothelial cells, connective tissue beams and extracellular matrix and that is responsible for a majority of the resistance to aqueous humor outflow through the anterior chamber angle. In a healthy eye, the aqueous humor under resistance from the structures of the eye, notably the trabecular meshwork, generates normal IOP in a range from about 12-20 mmHg.

When aqueous humor cannot drain normally from the anterior chamber of an eye, an animal can develop one of a family of ophthalmologic disorders characterized by above-normal IOP and gradual neuropathy caused in some manner by increased pressure on the optic nerve. Pressure increase begins in the anterior chamber of the eye and extends to the other parts of the eye, including the posterior chamber. Under the force of the IOP, a posterior segment compresses and destroys nerve fibers and blood vessels of the optic nerve. Such disorders can lead to gradual visual impairment and are collectively referred to as glaucoma.

Of particular interest is steroid-induced glaucoma. In steroid-induced glaucoma, aqueous humor builds up in the anterior chamber because it cannot flow through the trabecular meshwork, thereby increasing IOP. The exact pathophysiology of steroid-induced glaucoma is unknown, but it is known that steroids can increase or decrease transcription of genes, including genes of the trabecular meshwork cells. Ishibashi T., et al., "cDNA microarray analysis of gene expression changes induced by dexamethasone in cultured human trabecular meshwork cells," Invest. Ophthalmology & Visual Sci. 43:3691-3697 (2002). Other putative mechanisms for steroid-induced glaucoma include the following: (1) increased accumulation or deposition of extracellular matrix material, (2) decreased protease and stromelysin activities, (3) reorganization of the trabecular meshwork cytoskeleton, (4) increased nuclear size and DNA content, (5) decreased phagocytic activity, and (6) changes in expression of genes that encode specific proteins such as myocilin. Ishibashi, supra. See also Clark A., et al., "Glucocorticoid-induced formation of cross-linked actin networks in cultured human trabecular meshwork cells," Invest. Ophthalmology & Visual Sci. 35:281-294 (1994); Zhou L., et al., "Glucocorticoids effects on extracellular matrix proteins and integrins in bovine trabecular meshwork cells in relation to glaucoma," International Journal of Molecular Medicine 1:339-346 (1998); Clark A., et al., "Dexamethasone alters F-actin architecture and promotes cross-linked actin network formation in human trabecular meshwork tissue," Cell Motility & the Cytoskeleton 60:83-95 (2005); Wordinger R. & Clark A., "Effects of Glucocorticoids on the trabecular meshwork: towards a better understanding of glaucoma," Progress in Retinal and Eye Research 18:629-667 (1999); Dickerson J., et al., "The effect of dexamethasone on integrin and laminin expression in cultured human trabecular meshwork cells," Experimental Eye Research 66:731-738 (1998); and Cheng S., et al., "Regulation of avb3 and avb5 integrins by dexamethasone in normal human osteoblastic cells," Journal of Cellular Biochemistry 77:265-276 (2000), each of which is incorporated herein by reference as if set forth in its entirety.

Interestingly, steroid-induced glaucoma occurs only in a subpopulation of subjects receiving steroid therapy. About 40% of subjects receiving steroids experience an increase in IOP, which in most cases diminishes after therapy ceases. These subjects are called "steroid responders." Some steroid responders, about 4% to 6%, develop sustained elevated IOP, leading to chronic glaucoma. Steroid-induced glaucoma typically occurs after three to six weeks of steroid use, but in some cases may occur earlier.

In vitro, cultured trabecular meshwork cells or eye organ cultures treated with steroids and cultured trabecular meshwork cells from glaucomatous subjects show a cytoskeletal change in which actin in the trabecular meshwork cells adopts a cross-linked configuration. The cross-linked configuration is referred to as cross-linked actin networks (CLANs) and may make cells more rigid and less responsive to changes in outflow or pressure. CLAN formation is regulated by signaling mechanisms mediated by integrin receptors located on the plasma membrane of mammalian cells. Eye organ cultures are considered by the skilled artisan to be a reliable model system for studying in vivo mammalian eyes and for evaluating therapies for in vivo effectiveness.

Integrins are large glycoproteins having non-covalently linked α- and β-subunits. Integrins are found on virtually all human cells and transmit signals bi-directionally across a cell membrane. As cell surface receptors, integrins participate in a diverse array of biological functions including cellular development, cellular/tissue repair, angiogenesis, inflammation and hemostasis.

Integrin structures and functions are known in the art. See Alpin A., et al., "Signal transduction and signal modulation by cell adhesion receptors: the role of integrins, cadherins, immunoglobulin-cell adhesion molecules, and selectins," Pharmacological Reviews 50:197-263 (1998); and Brakebusch C. & Fässler R., "The integrin-actin connection, an eternal love affair," EMBO Journal 22:2324-2333 (2003), each of which is incorporated herein by reference as if set forth in its entirety. At least eighteen isoforms of the α-subunit and eight isoforms of the β-subunit combine to form more than twenty integrin heterodimers having α- and β-subunits. Human trabecular meshwork cells contain the following integrin subunits: α1, α3, α4, α5, α6, αv, β1, β3, β4 and β5. Zhou L., et al., "Expression of receptors in the human trabecular meshwork," Current Eye Research 19:395-402 (1999). Integrins bind a number of extracellular matrix proteins via an extracellular domain and intact with a variety of tyrosine kinases, adaptor proteins and actin binding proteins via a cytoplasmic tail.

Current treatments for glaucoma include pharmacological and surgical therapies, either alone or in combination. All treatments can have significant side effects. Pharmacological agents, most commonly administered as eye drops, can be used alone or in combination to decrease aqueous humor production or to improve aqueous humor outflow from the eye. β-adrenergic blockers such as timolol, levobunolol and betaxolol decrease aqueous humor production. Side effects of β-adrenergic blockers can include cardiac failure, heart block and bronchospasm. Cholinergic agonists such as pilocarpine, carbachol, and phospholine iodide improve outflow facility from the trabecular meshwork. Side effects of cholinergic agonists can include miosis, brow ache and decreased vision. Carbonic anhydrase inhibitors such as acetazolamide, dorzolamide and brinzolamide decrease aqueous humor production. Side effects of carbonic anhydrase inhibitors can include gastrointestinal upset, malaise, renal stones and aplastic anemia. Non-selective α-agonists such as epinephrine and dipivefrin decrease aqueous humor production and increase trabecular outflow facility. Side effects of a non-selective α-agonists can include pupil dilation, macular edema and tachycardia. Selective α-agonists such as apraclonidine and brimonidine decrease aqueous humor production and increase outflow through the uveoscleral pathway (an alternative, but less utilized, fluid exit pathway to the trabecular meshwork). Side effects of selective α-agonists can include contact allergy and hypotension. Prostaglandin agonists such as latanoprost, travoprost and bimatoprost improve uveoscleral outflow. Side effects of prostaglandins can include iris color change, lash growth and trichiasis. Hyperosmotics such as glycerin (po) and mannitol (iv) establish a concentration gradient that draws excess aqueous humor from the eye. Side effects of using hyperosmotics can include diuresis, cardiovascular overload, renal insufficiency, and stroke, so their use is limited to emergency situations.

When pharmacological agents are unsuccessful in open-angle glaucoma or when a subject presents with closed-angle glaucoma, invasive surgery is indicated. In argon laser trabeculoplasty (ALT), a laser beam is directed at the trabecular meshwork that increases aqueous humor drainage through a mechanism that is not well understood. In laser cyclophotocoagulation, thermal energy applied to the ciliary body destroys the tissue, thereby reducing aqueous humor production. Trabeculectomy establishes a flow route that bypasses the trabecular meshwork so that aqueous humor drains from the anterior chamber just beneath the conjunctiva, the outermost covering of the eye, on the surface of the eye where it is gradually absorbed by blood vessels or diffuses through the conjunctiva. Iridotomy, generally used for closed-angle glaucoma, employs a laser to make an incision in a peripheral area of the iris of the eye to establish a direct aqueous humor flow route between the anterior chamber and the posterior chamber. Iridectomy is similar to iridotomy, but does not employ a laser. In iridotomy, a small section of peripheral iris is surgically excised.

Glaucoma is an increasingly important public health concern, especially in view of the aging of the population. No current treatment satisfactorily and fully addresses onset and control of glaucoma, particularly the particular aspects of steroid-induced glaucoma. In addition, steroids are an effective therapeutic agent in many human diseases, but they can cause unfortunate side effects in a minority of subjects susceptible to steroid-induced glaucoma. Thus, there is a need to develop methods to prevent and treat steroid-induced glaucoma to permit the continued use of steroids as a therapeutic.

SUMMARY OF THE INVENTION

In the presence of a steroidal agent, cultured trabecular meshwork cells produce ligands (such as fibronectin and laminin) that interact specifically with β1 and β3 integrins such as αvβ3, α4β1, and α5β1 integrins. These steroid-induced activators may upregulate expression of β3 integrin and interact with β1 integrin to promote CLAN formation. This observation suggests that in a subject treated with a steroidal agent a method for reducing or preventing CLAN formation includes the step of interrupting the signaling pathways that upregulate β3 integrin expression.

In one aspect, the method includes the step of treating an eye of a subject experiencing or susceptible to steroid-induced CLAN formation with an integrin antagonist (inhibitor) that interferes with binding of a steroid-induced activator to the integrin or an integrin antagonist that interferes with signal transduction to the interior of trabecular meshwork cells, where the antagonist is administered in an amount effective to reduce or prevent CLAN formation. Certain integrin inhibitors have been mentioned as agents for treating eye diseases, especially for treating neovascular glaucoma, a highly specialized form of glaucoma wherein blood vessels grow into or around the trabecular meshwork, but as far as applicants are aware, integrin inhibitors have not been considered to treat or prevent CLANs associated with steroid-induced glaucoma. Neovascular glaucoma and steroid-induced glaucoma are distinct conditions.

At present, one cannot ascertain with certainty whether a subject is sufficiently sensitive to therapeutic steroids to be susceptible to steroid-induced glaucoma or CLAN formation, but one can administer to all steroid therapy patients a prophylactic amount of an integrin antagonist in combination with the steroid therapy to proactively prevent CLAN formation during or after the steroid therapy. Accordingly, in a second aspect, a method for administering a steroidal agent to a subject in need of steroid therapy includes the step of co-administering with the steroidal agent an integrin antagonist in an amount sufficient to reduce or prevent CLAN formation, the amount being an amount effective to reduce or prevent CLAN formation in subjects experiencing steroid-induced CLAN formation.

In some embodiments, the CLAN formation is associated with steroid-induced glaucoma.

In some embodiments, the integrin antagonist can be an anti-αvβ3 antibody, an anti-αv antibody, an anti-α4β1 antibody, an anti-α4 antibody, an anti-α5β1 antibody or an anti-α5 antibody. In some embodiments, the antagonist is a cytoplasmic tyrosine kinase inhibitor, such as an inhibitor of a Src family kinase (Src, Yes, Fgr, Yrk, Fyn, Lyn, Hck, Lck and Blk) and preferably a Src kinase inhibitor. The Src family kinase inhibitor can be PP2.

In some embodiments, the eye is treated directly with an integrin antagonist, for example by administering the agent to the trabecular meshwork.

In some embodiments, the method also includes the step of quantifying the reduction in CLAN formation from the provision of the integrin antagonist. The quantifying step can include the steps of measuring intraocular pressure (IOP) reduction or aqueous humor outflow from the eye before and after the treating step.

It is an object in certain embodiments to reduce or eliminate CLAN structures, or to prevent formation of CLAN structures, in trabecular meshwork cells in a human or non-human mammalian subject.

It is an object in certain embodiments to reduce or prevent CLAN formation in trabecular meshwork cells of a subject experiencing or susceptible to steroid-induced glaucoma.

These and other objects, aspects and advantages of the present invention will become better understood from the description that follows. The description of preferred embodiments is not intended to limit the invention to cover all modifications, equivalents and alternatives. Reference should therefore be made to the claims herein for interpreting the scope of the invention.

BRIEF DESCRIPTION OF THE DRAWINGS

Not applicable.

DETAILED DESCRIPTION OF THE INVENTION

The methods of the invention can be practiced on an eye of a human or non-human mammalian subject experiencing or susceptible to formation of CLANs in trabecular meshwork cells that contain integrins having a $\beta 1$ or a $\beta 3$ subunit.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

As used herein, a sufficient amount is an amount of an agent that reduces the number of trabecular meshwork cells having CLAN structures by at least two to four fold in an eye of a subject having steroid-associated CLAN structures. An amount of an agent is also considered effective if a reduction in CLAN structures is measured as an increase in aqueous humor outflow from the treated eye. Similarly, a prophylactic amount of an agent co-administered with a steroidal agent is effective either if the subject does not develop CLANs or if there is no steroid-induced reduction in aqueous humor outflow.

The antagonist can be administered alone or in combination with another antagonist to treat or to prevent steroid-induced glaucoma. It is contemplated that co-administration or contemporaneous administration of the integrin antagonist(s) and the therapeutic steroid can prevent CLAN formation in a subject susceptible to developing steroid-induced glaucoma.

A suitable integrin antagonist blocks or inhibits the activity of an integrin. An antagonist interferes with an ability of a natural ligand to bind to an integrin or to transduce a signal to the interior of a cell. Shimaoka M. & Springer T., "Therapeutic antagonists and conformational regulation of integrin function," Nat. Rev. Drug Discov. 2:703-716 (2003), incorporated herein by reference as if set forth in its entirety, reviews the art of integrin antagonists, with focus on the various antagonist classes and with reference in the review's FIG. 8 legend to the original papers that describe such antagonists. As in the case of an integrin agonist, an integrin antagonist can either bind to an integrin itself or can modulate production, structure or activity of the integrin's ligand, thereby antagonizing the activity of the integrin.

An integrin antagonist can be, e.g., an antibody or fragment of an antibody, which can be a monoclonal antibody, a peptide, such as an RGD peptide, especially a modified RGD sequence such as cyclo-RGDSPA, cyclo-ARGD-aminomethylbenzoyl or cyclo-G-penicillin-GRGDSPCA, or a non-peptide chemical mimetic. Suitable antagonists of $\alpha v \beta 3$ integrin are described, e.g., in Mousa S., "$\alpha_v$ vitronectin receptors in vascular-mediated disorders," Med. Res. Reviews 23:190-199 (2003), incorporated herein by reference as if set forth in its entirety. Similarly, an antibody integrin antagonist to $\alpha v \beta 3$ integrin is described, e.g., in Gutheil J. et al., "Targeted anti-angiogenic therapy for cancer using vitaxin: a humanized monoclonal antibody to the integrin $\alpha_v \beta_3$," Clin. Cancer Res. 6:3056-3061 (2000), incorporated herein by reference as if set forth in its entirety. It is also possible to prevent expression of integrins using siRNA or dominant negative constructs having only integrin cytoplasmic tails.

Other suitable integrin antagonists are inhibitors that can interfere with a downstream signaling event mediated by integrins. Of particular interest are inhibitors of Src family tyrosine kinases, particularly Src kinase. A suitable inhibitor of Src kinase is PP2 (Calbiochem), although antibodies (Abcam; Cambridge, Mass.) and siRNA are also suitable inhibitors.

Preferred routes of delivery of the integrin antagonist are topical or intravenous. The skilled artisan will appreciate the desirability of non-invasive administration of the antagonist. Accordingly, eye drops are a preferred delivery vehicle and, when this route is employed, use of small molecules or peptides are preferred to full-length proteins, including antibodies.

An example below demonstrates that cultured human trabecular meshwork cells develop CLAN structures when exposed to steroids or when exposed to an integrin agonist that stimulates or enhances the activity of an $\alpha 5 \beta 1$, $\alpha 4 \beta 1$ or $\alpha v \beta 3$ integrin. Conversely, inhibition of integrin signaling in trabecular meshwork cells via administration of an integrin antagonist attenuates CLAN formation such that actin is maintained in a normal cytoskeletal structure or reorganized from CLAN structures to normal actin cytoskeleton.

The invention will be more fully understood upon consideration of the following Examples.

EXAMPLES

Example 1 (Working)

Integrin Agonist Induces CLAN Formation in Cultured Cells

Cultured, diploid human trabecular meshwork cells obtained from trabecular meshwork explants were plated on coverslips coated with extracellular matrix materials, including poly-L-lysine (20 nM in PBS), fibronectin (100 nM in PBS), type I collagen (20 nM in PBS), type IV collagen (20 nM in PBS), vitronectin (20 nM in PBS), vascular cell adhesion molecule (VCAM-1, an $\alpha 4 \beta 1$ ligand; 20 nM in PBS), fibronectin III$_{7-10}$ domain (an $\alpha 5 \beta 1$ ligand; 20 nM in PBS), fibronectin III$_{12-14}$ domain (20 nM in PBS), or fibronectin IICS domains (20 nM in PBS), or activating antibodies to $\beta 1$ (anti-B3B11; Chemicon Int'l, Inc.; Temecula, Calif.; 10 µg/ml), $\beta 3$ (anti-AP-5; The Blood Center of Southeastern Wisconsin; Milwaukee, Wis.; 8 µg/ml), or $\alpha 2 \beta 1$ (anti-JBS2; Chemicon Int'l, Inc.; 6 µg/ml) integrins. In experiments using antibodies as substrates, coverslips were pre-coated with 1:100 unconjugated goat anti-mouse IgG (Jackson Immunoresearch, Inc.; West Grove, Pa.). In some instances, anti-$\beta 3$ antibodies were used as soluble ligands. The trabecular meshwork cells were allowed to spread on the coverslips for three hours at 37° C., 95% humidity and ambient air, 8% $CO_2$.

CLAN formation was assessed by immunofluorescence microscopy. CLANs were labeled with either Alexa 488 phalloidin (Molecular Probes; Eugene, Oreg.) or polyclonal anti-F-actin (Sigma-Aldrich; St. Louis, Mo.). Anti-F-actin was detected using either Alexa 488 conjugated goat anti-rabbit IgG or Alexa 488 conjugated donkey anti-rabbit IgG. All monoclonal antibodies were detected using Alexa 546 conjugated goat anti-mouse IgG. Fluorescence was observed with a Zeiss Axioplan 2 microscope equipped with an Axiocam Hrm camera and Axiovision 3.1 software.

The adsorbed fibronectin and anti-β1 antibody induced CLAN formation in 13% and 11% of the cells, respectively. In contrast, type I collagen and type IV collagen induced CLAN formation by 4-5%. VACM-1 induced CLAN formation in 13% and the $III_{7-10}$ fibronectin fragment induced formation in 7% of the cells. Poly-L-lysine, the $III_{7-10}$ and IIICS fragments of fibronectin, adsorbed α2β1—and adsorbed β3 integrin antibodies all failed to induce CLAN formation in trabecular meshwork cells.

Soluble β3 antibody alone increased CLAN formation in 5.5% of trabecular meshwork cells. In addition, soluble β3 antibody increased CLAN formation in trabecular meshwork cells by two- and ten-fold on cells spread on adsorbed β1 or α2β1 antibodies when compared to trabecular meshwork cells spread on only absorbed β1 or α2β1 antibodies. The increases in CLAN formation observed with the soluble β3 antibody and absorbed α2β1 antibody, however, were not greater than soluble β3 antibodies alone. Furthermore, soluble β3 antibody increased CLAN formation by three- and four-fold in trabecular meshwork cells spread on VCAM-1 and the fibronectin $III_{7-10}$ domain. Finally, soluble β3 antibody increased CLAN formation in trabecular meshwork cells by two fold (to 23%) when provided to cells spread on anti-β1 antibody.

These studies show that CLAN formation may be regulated by specific integrin signaling pathways involving β1 and β3 integrins, suggesting that integrin co-signaling via β1 and β3 contributes to the pathophysiology of steroid-induced glaucoma and modulates outflow facility in general through its regulation of the actin cytoskeleton in trabecular meshwork cells.

Example 2 (Working)

Src Family Tyrosine Kinase Inhibitor Reduces Clan Formation in Cultured Cells

Trabecular meshwork cells were cultured as in Example 1 on fibronectin-coated cover slips in the absence and presence of soluble anti-β3. Prior to plating, a group of trabecular meshwork cells were pre-treated with an inhibitor of Src kinase, PP2 (20 μM; Calbiochem) for thirty to sixty minutes. The treated cells were then plated in the presence of PP2. Control cells were untreated. In the absence of soluble anti-β3, PP2 reduced CLAN formation compared to control cells (from 10% to 0%). In the presence of soluble anti-β3, PP2 also reduced CLAN formation compared to control cells (from 30% to 1%). These studies show that Src kinase inhibitors nearly eliminate CLAN formation, even in the presence of an integrin stimulus.

Example 3 (Prophetic)

Integrin Agonist Induces Clan Formation in Human or Monkey Anterior Chambers

Matched pairs of human or monkey anterior chambers are obtained from cadavers. Anterior chambers are mounted according to the procedure disclosed in Johnson D. & Tschumper R., "Human trabecular meshwork organ culture. A new method," Invest. Ophthalmol. Vis. Sci., 28:945-953 (1987). See also Hu Y., et al., "Monkey organ-cultured anterior segments: technique and response to H-7," Exp. Eye Res. (Jan. 26, 2006) [Epub ahead of print], incorporated herein by reference as if set forth in its entirety.

Once mounted for study and after baseline outflow facility has been determined from both eyes, peptide agonists for αvβ3 and α4β1 integrins (Table 1) are perfused into the anterior chamber of one human (or monkey) eye in culture. Control peptides have either a G to A substitution or a D to Q substitution in the RGD sequence. Alternatively, integrin-activating antibodies (Table 2) may be perfused into the anterior chamber of one human (or monkey) eye in culture. The other paired eye serves as a control and receives only buffer or a control peptide. The concentration of the peptides and the duration of the treatment are varied to generate a dose and time dependent response curve. The eyes in cultures are continuously perfused with the peptide for one to two days. Optionally, the peptide is washed out and perfusion continued for at least another twenty-four hours to see how well the eye recovers. Outflow facility measurements on all eye organ cultures monitors corresponding changes in outflow facility. Upon histological examination, it is observed that agonist peptides induce CLAN formation in treated eyes.

TABLE 1

Integrin Agonists

| Integrin | Peptide | Function | Concentration |
|---|---|---|---|
| αvβ3 | Cyclo-G-pen-GRGDSPLA | Agonist | 0.7 mM |
| αvβ3 | Cyclo-ARGD-3-aminomethyl benzoyl | Agonist | 100 pM |
| α4β1 | QIDS | Agonist | 1 μg/ml |
| α4 | Cyclo-CQIDSPC | Agonist | 0.2 mM |
| α5β1 | Cyclo-RGDSPA | Agonist | 0.223 μM |

TABLE 2

Integrin-Activating Antibodies

| Integrin | Antibody Name | Activity | Effective Concentration |
|---|---|---|---|
| αvβ3 | AP5 | Activating | 8-10 μg/ml |
| α4β1 | HP2/1 | Activating | 10-50 μg/ml |
| α5β1 | AP5 | Activating | 10-50 μg/ml |

Example 4 (Prophetic)

Integrin Antagonist Reduces CLAN Formation in Human or Monkey Anterior Chambers Treated with Steroid Human or monkey anterior chambers are obtained and mounted as described above. Once mounted for study and after baseline outflow has been determined from both eyes, a steroid such as $10^{-7}$ M dexamethasone in 0.1% ethanol is administered to the anterior eye chambers for a time sufficient to induce decreases in outflow facility in ~45% of the eyes for 7-10 days. An IOP increase of >5 mm Hg from baseline during the treatment is considered a response to the steroid, as previously defined (Clark et al., supra). A peptide antagonist (Table 3) is perfused along with the steroid into one eye and is present throughout the study. Alternatively, integrin-blocking antibodies (Table 4) are perfused with the steroid into one eye in culture. The other eye is only treated with the steroid. Following the treatment, no decrease in outflow facility relative to baseline is noted in the eye that received both the steroid and the antagonist, whereas decreased outflow facility is observed in the eye treated only with the steroid.

TABLE 3

Integrin Antagonists

| Integrin | Peptide | Function | Concentration |
|---|---|---|---|
| $\alpha v\beta 3$ | Cyclo-ARGD-3-aminomethyl benzoyl | Antagonist | 10 μM |
| $\alpha v\beta 3$ | Cyclo-G-pen-GRGDSPCA | Antagonist | 0.2 mM |
| $\alpha 4\beta 1$ | (4-((2-methylphenyl)aminocarboxylaminophenyl acetyl-ILDV | Antagonist | 4 nM |
| $\alpha 5\beta 1$ | GRGD-D-SP | Antagonist | 0.2 nM |
| $\alpha 5\beta 1$ | Ac-PHSCN-NH$_2$ | Antagonist | 1.0 μM |

TABLE 4

Integrin-Blocking Antibodies

| Integrin | Antibody Name | Activity | Effective Concentration |
|---|---|---|---|
| $\alpha v\beta 3$ | LM609 | Blocking | 100 μg/ml |
| $\alpha v$ | M9 | Blocking | 10-50 μg/ml |
| $\alpha 4\beta 1$ | HP1/2 | Blocking | 10-50 μg/ml |
| $\alpha 4$ | P1H4 | Blocking | 10-50 μg/ml |
| $\alpha 5\beta 1$ | HA5 | Blocking | 10-50 μg/ml |
| $\alpha 5\beta 1$ | JBS5 | Blocking | 10-50 μg/ml |
| $\alpha 5$ | P1D6 | Blocking | 10-50 μg/ml |

Example 5 (Prophetic)

CLAN Interfering Agent Reduces CLAN Formation in Human or Monkey Anterior Chambers Treated with Steroid Human or monkey anterior chambers are obtained and mounted as described above. Once mounted for study and after baseline outflow has been determined from both eyes, a steroid such as $10^{-7}$ M dexamethasone in 0.1% ethanol is administered to the anterior eye chambers for a time sufficient to induce decreases in outflow facility in ~45% of the eyes for 7-10 days. An IOP increase of >5 mm Hg from baseline during the treatment is considered a response to the steroid, as previously defined (Clark et al., supra). A Src family kinase inhibitor is perfused along with the steroid into one eye and is present throughout the study. The other eye is only treated with the steroid. Following the treatment, no decrease in outflow facility relative to baseline is noted in the eye that received both the steroid and the agent, whereas decreased outflow facility is observed in the eye treated only with the steroid.

Example 6 (Prophetic)

Integrin Agonist Reduces Outflow Facility from Eyes of a Monkey

A baseline IOP (or baseline outflow facility) is determined in a non-human animal such as a male or female adolescent or young adult Cynomolgus (*Macaca fascicularis*) or rhesus (*Macaca mulatta*) monkey for forty-five minutes. Using a conventional apparatus and conventional delivery methods, an integrin agonist peptide (Table 1) or integrin-activating antibody (Table 2) is administered to an eye of the animal. The agonist is administered for a time and in an amount effective to raise the IOP to a level above the normal level. Outflow facility is subsequently measured for forty-five to ninety minutes to provide optimum mixing and maintenance of anterior chamber "drug" levels, while minimizing perfusion-induced resistance washout and degradation of the normal physiology. Total outflow facility is measured by two-level constant pressure perfusion using Bárány's perfusate. Upon completion of the delivery and measurement regimen, an increased IOP is observed in a treated eye relative to the pre-treatment pressure.

If longer treatments are needed to see an effect, peptides are introduced into the anterior chamber by a 10 μl bolus injection every four to six hours since washout from normal outflow can lead to a rapid removal of the peptide. Peptides are injected using a 30 gauge needle introduced under microscopic control by threading the bevel through the cornea for several mm before entering the anterior chamber, such that no fluid is lost when the needle is removed and no inflammation is produced. The peptides are injected transcorneally, as anesthesia cannot be maintained for such an extended period (twenty-four hours), and full perfusions cannot be done at such close intervals. For these studies, baseline outflow facility measurements are not made. Rather, monkeys are selected for trials if they have undergone at least two previous outflow facility experiments and in which the most recent baseline outflow facility measurements were similar in both eyes.

This example corresponds in vivo to Example 1 in vitro and is a proof of concept, especially when taken in conjunction with the results of other Examples. It is observed that the treated population has an increased occurrence of CLAN structures, and reduced aqueous humor outflow facility, than the control population. However, for the reasons noted above, these trials are complex and expensive.

The skilled artisan will appreciate the difficulties associated with in vivo administration of a steroid and an integrin agonist, namely the number of monkeys involved (for both subjects and controls) and the time and frequency of treatment required to observe an increase in IOP in subject monkeys make the procedure possible, but difficult to carry out absent substantial resources and facilities. Further, as it is not now known how to determine which animal is susceptible to steroid-induced glaucoma, the skilled artisan can develop a population-based experimental protocol in which a statistically-relevant number of cases of steroid induced-glaucoma would be expected in the treated and control populations. However, for the reasons noted above, these trials are complex and expensive.

Example 7 (Prophetic)

Integrin Antagonist Increases Outflow Facility from Eyes of a Non-Human or Human Animal Previously Treated with a Steroid A baseline IOP (or baseline outflow facility) is determined in a non-human animal as described in Example 6 except the animal is previously treated with an amount of a steroid to increase IOP. Using a conventional apparatus and conventional delivery methods, an integrin antagonist peptide (Table 3) or integrin-blocking antibody (Table 4) is administered to an eye of the animal. The antagonist or antibody is administered for a time and in an amount effective to lower the IOP to a level at or below the normal level. Outflow facility is subsequently measured for forty-five to ninety minutes to provide optimum mixing and maintenance of anterior chamber "drug" levels, while minimizing perfusion-induced resistance washout and degradation of the normal physiology. Total outflow facility is measured by two-level constant pressure perfusion using Bárány's perfusate. Upon completion of the delivery and measurement regimen, an decreased IOP is observed in a treated eye relative to the pre-treatment pressure.

If longer treatments are needed to see an effect, antagonist or antibodies are introduced into the anterior chamber by a 10 μl bolus injection every four to six hours since washout from normal outflow can lead to a rapid removal of the peptide. Antagonist and antibodies are injected using a 30 gauge needle introduced under microscopic control by threading the bevel through the cornea for several mm before entering the anterior chamber, such that no fluid is lost when the needle is removed and no inflammation is produced. The antagonist or antibodies are injected transcorneally, as anesthesia cannot be maintained for such an extended period (twenty-four hours), and full perfusions cannot be done at such close intervals. For these studies, baseline outflow facility measurements are not made. Rather, monkeys are selected for trials if they have undergone at least two previous outflow facility experiments and in which the most recent baseline outflow facility measurements were similar in both eyes.

It is observed that the treated population has a reduced occurrence of CLAN structures, and greater aqueous humor outflow facility, than the control population.

Example 8 (Prophetic)

Src Kinase Inhibitor Increases Outflow Facility from Eyes of a Mammalian Non-Human or Human Animal Previously Treated with a Steroid A baseline IOP (or baseline outflow facility) is determined in an animal as described in Example 6 except the animal is previously treated with an amount of a steroid to increase IOP. Using a conventional apparatus and conventional delivery methods, a Src family tyrosine kinase inhibitor is administered to an eye of the animal. The inhibitor is administered for a time and in an amount effective to lower the IOP to a level at or below the normal level, as established in prior eye organ culture trials. Outflow facility is subsequently measured for forty-five to ninety minutes to provide optimum mixing and maintenance of anterior chamber "drug" levels, while minimizing perfusion-induced resistance washout and degradation of the normal physiology. Total outflow facility is measured by two-level constant pressure perfusion using Bárány's perfusate. Upon completion of the delivery and measurement regimen, an decreased IOP is observed in a treated eye relative to the pre-treatment pressure.

If longer treatments are needed to see an effect, the inhibitor is introduced into the anterior chamber by a 10 μl bolus injection every four to six hours since washout from normal outflow can lead to a rapid removal of the peptide. The inhibitor is injected using a 30 gauge needle introduced under microscopic control by threading the bevel through the cornea for several mm before entering the anterior chamber, such that no fluid is lost when the needle is removed and no inflammation is produced. The inhibitor is injected transcorneally, as anesthesia cannot be maintained for such an extended period (twenty-four hours), and full perfusions cannot be done at such close intervals. For these studies, baseline outflow facility measurements are not made. Rather, monkeys are selected for trials if they have undergone at least two previous outflow facility experiments and in which the most recent baseline outflow facility measurements were similar in both eyes.

It is observed that the treated population has a reduced occurrence of CLAN structures, and greater aqueous humor outflow facility, than the control population.

Example 9 (Prophetic)

Integrin Antagonist Co-Administered with a Steroid Maintains or Increases Outflow Facility from an Eye of a Non-Human or Human Animal A baseline IOP (or baseline outflow facility) is determined in an animal as described above. Using a conventional apparatus and conventional delivery methods, a steroid (e.g. dexamethasone) and an integrin antagonist peptide (Table 3) or integrin-blocking antibody (Table 4) are administered to an eye of the animal. Some animals are administered steroid only. The antagonist or antibody is administered for a time and in an amount effective to maintain the IOP to a level at or below the normal level. Outflow facility is subsequently measured for forty-five to ninety minutes to provide optimum mixing and maintenance of anterior chamber "drug" levels, while minimizing perfusion-induced resistance washout and degradation of the normal physiology. Total outflow facility is measured by two-level constant pressure perfusion using Bárány's perfusate. Upon completion of the delivery and measurement regimen, a similar or decreased IOP is observed in a treated eye relative to the pre-treatment pressure.

If longer treatments are needed to see an effect, antagonist or antibodies are introduced into the anterior chamber by a 10 μl bolus injection every four to six hours since washout from normal outflow can lead to a rapid removal of the peptide. Antagonist and antibodies are injected using a 30 gauge needle introduced under microscopic control by threading the bevel through the cornea for several mm before entering the anterior chamber, such that no fluid is lost when the needle is removed and no inflammation is produced. The antagonist or antibodies are injected transcorneally, as anesthesia cannot be maintained for such an extended period (twenty-four hours), and full perfusions cannot be done at such close intervals. For these studies, baseline outflow facility measurements are not made. Rather, monkeys are selected for trials if they have undergone at least two previous outflow facility experiments and in which the most recent baseline outflow facility measurements were similar in both eyes.

It is observed that the antagonist-treated population maintained or increased aqueous humor outflow facility compared to the steroid-treated population.

Example 10 (Prophetic)

Src Kinase Inhibitor Co-Administered with a Steroid Maintains or Increases Outflow Facility from Eyes of a Non-Human or Human Animal A baseline IOP (or baseline outflow facility) is determined in a non-human animal as described above. Using a conventional apparatus and conventional delivery methods, a steroid (e.g. dexamethasone) and a Src family tyrosine kinase inhibitor is administered to an eye of the animal. Some animals are administered steroid only. The inhibitor is administered for a time and in an amount effective to maintain or lower the IOP to a level at or below the normal level, as established in prior eye organ culture trials. Outflow facility is subsequently measured for forty-five to ninety minutes to provide optimum mixing and maintenance of anterior chamber "drug" levels, while minimizing perfusion-induced resistance washout and degradation of the normal physiology. Total outflow facility is measured by two-level constant pressure perfusion using Bárány's perfusate. Upon completion of the delivery and measurement regimen, a similar or increased IOP is observed in a treated eye relative to the pre-treatment pressure.

If longer treatments are needed to see an effect, the inhibitor is introduced into the anterior chamber by a 10 μl bolus injection every four to six hours since washout from normal outflow can lead to a rapid removal of the peptide. The inhibitor is injected using a 30 gauge needle introduced under microscopic control by threading the bevel through the cornea for several mm before entering the anterior chamber, such that no fluid is lost when the needle is removed and no inflammation is produced. The inhibitor is injected transcorneally, as anesthesia cannot be maintained for such an extended period (twenty-four hours), and full perfusions cannot be done at such close intervals. For these studies, baseline outflow facility measurements are not made. Rather, monkeys are selected for trials if they have undergone at least two previous outflow facility experiments and in which the most recent baseline outflow facility measurements were similar in both eyes.

It is observed that the inhibitor-treated population maintained or increased aqueous humor outflow facility compared to the steroid-treated population.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set for by the appended claims.

The invention claimed is:

1. A method for treating an eye of a human or non-human mammalian animal receiving or having received steroidal treatment, the method comprising the steps of:
treating the eye with an agent that reduces or prevents cross-linked actin network (CLAN) formation in an amount sufficient to reduce or prevent CLAN formation, wherein the agent is an integrin antagonist selected from the group consisting of an antibody and a Src family tyrosine kinase inhibitor.

2. A method as claimed in claim 1, wherein the integrin antagonist is selected from the group consisting of anti-αvβ3 antibody, anti-αv antibody, anti-α4β1 antibody, anti-α4 antibody, anti-α5β1 antibody and anti-α5 antibody.

3. A method as claimed in claim 1, wherein the integrin antagonist is a Src kinase inhibitor.

4. A method as recited in claim 3, wherein the Src kinase inhibitor is PP2.

5. A method as claimed in claim 1, wherein agent is administered to trabecular meshwork cells of the eye.

6. A method as claimed in claim 1, further comprising the step of quantifying a reduction in CLAN formation resulting from the provision of the integrin antagonist.

7. A method as claimed in claim 6, the quantifying step further comprising a step selected from the group consisting of measuring intraocular pressure reduction and measuring aqueous humor outflow from the eye before and after the treating step.

8. A method as claimed in claim 1, wherein the agent is co-administered with the steroidal treatment.

9. A method for treating an eye of a human or non-human mammalian animal receiving or having received steroidal treatment, the method comprising the steps of:
treating the eye with an integrin antagonist that reduces or prevents cross-linked actin network (CLAN) formation selected from the group consisting of an antibody and a Src family tyrosine kinase inhibitor in an amount sufficient to reduce or prevent CLAN formation; and
quantifying a reduction in CLAN formation resulting from the provision of the integrin antagonist.

* * * * *